(12) United States Patent
Birtwhistle et al.

(10) Patent No.: US 10,003,545 B2
(45) Date of Patent: Jun. 19, 2018

(54) MOBILE PHONE APPLICATION FOR DIABETES CARE WITH MEDICAL FEATURE ACTIVATION

(71) Applicant: Roche Diagnostics Operations, Inc., Indianapolis, IN (US)

(72) Inventors: Daniel Birtwhistle, Fishers, IN (US); Eric S. Carlsgaard, Zionsville, IN (US); Michael L. Flis, Carmel, IN (US); Kevin J. Friedman, Indianapolis, IN (US); Hans P. Jensen, Fishers, IN (US); David B. Markisohn, Indianapolis, IN (US); Robert E. Reinke, Indianapolis, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 628 days.

(21) Appl. No.: 14/172,099

(22) Filed: Feb. 4, 2014

(65) Prior Publication Data
US 2014/0325065 A1 Oct. 30, 2014

Related U.S. Application Data

(60) Provisional application No. 61/816,564, filed on Apr. 26, 2013.

(51) Int. Cl.
*H04L 12/24* (2006.01)
*H04L 12/911* (2013.01)
(Continued)

(52) U.S. Cl.
CPC .......... *H04L 47/70* (2013.01); *G06F 19/3468* (2013.01); *G06F 21/121* (2013.01);
(Continued)

(58) Field of Classification Search
CPC ...... H04L 12/911; H04L 47/70; G06F 21/121; G06F 2221/2137; G06F 2221/2151; G06F 19/3468; G06F 19/3412
(Continued)

(56) References Cited

U.S. PATENT DOCUMENTS 7,231,549 B1 * 6/2007 Rhea .................. G06F 11/2294
714/25
8,577,334 B1 * 11/2013 Smith .................. H04W 12/08
455/410

(Continued)

FOREIGN PATENT DOCUMENTS

WO 2009/071188 A1 6/2009

*Primary Examiner* — Moustafa M Meky
*Assistant Examiner* — Elizabeth Kassa
(74) *Attorney, Agent, or Firm* — Harness Dickey

(57) ABSTRACT

A method for activating a physician-prescribable feature of an application program executed on a mobile device is disclosed. The method includes receiving, by the application program, an activation code to activate a feature of the application program and one or more parameters associated with a prescription. The method includes transmitting, by the application program, the activation code to a server and receiving an authorization code from the server, where the authorization code indicates a validity of the activation code. The method includes activating, by the application program, the feature using the activation code, the activation being performed in response to the activation code being valid; configuring, by the application program, the activated feature using at least one of the one or more parameters associated with the prescription; and generating, using the activated feature, data based on the one or more parameters associated with the prescription.

16 Claims, 9 Drawing Sheets

(51) Int. Cl.
    *G06F 19/00*     (2018.01)
    *G06F 21/12*     (2013.01)

(52) U.S. Cl.
    CPC ..... *G16H 40/40* (2018.01); *G06F 2221/2137* (2013.01); *G06F 2221/2151* (2013.01)

(58) Field of Classification Search
    USPC .......................................................... 709/225
    See application file for complete search history.

(56) References Cited

U.S. PATENT DOCUMENTS

| | | | |
|---|---|---|---|
| 2005/0289072 A1* | 12/2005 | Sabharwal | G06F 21/121 |
| | | | 705/59 |
| 2008/0201325 A1* | 8/2008 | Doniger | G06F 19/3468 |
| 2009/0150831 A1* | 6/2009 | Young | G06Q 50/22 |
| | | | 715/845 |
| 2010/0198142 A1 | 8/2010 | Sloan et al. | |
| 2011/0124996 A1* | 5/2011 | Reinke | A61M 5/14248 |
| | | | 600/365 |
| 2012/0096451 A1* | 4/2012 | Tenbarge | G06F 11/1433 |
| | | | 717/170 |
| 2012/0232520 A1* | 9/2012 | Sloan | A61B 5/14532 |
| | | | 604/504 |
| 2013/0254125 A1* | 9/2013 | Sanders | H04L 63/102 |
| | | | 705/310 |
| 2013/0333006 A1* | 12/2013 | Tapling | G06F 21/42 |
| | | | 726/6 |

* cited by examiner

| Basic Settings | Default |
| --- | --- |
| 1. Target Range | 3.9-6.1 mmol/L |
| 2. Meal Rise | 3.9 mmol/L |
| 3. Carb Ratio | 1 U: _____ g |
| 4. Insulin Sensitivity | 1 U: _____ mmol/L |
| 5. Max Bolus | 25 U |
| Additional Settings | |
| 6. Snack Size | 0 g |
| 7. Bolus Insulin Name | Generic Bolus (Rapid-acting) |
| 8. Offset Time | 1 hour |
| 9. Acting Time | 4 hours |
| 10. Insulin Increment | 1U |
| Related Settings | |
| 11. Hypo | 3.9 mmol/L |

FIG. 9

MOBILE PHONE APPLICATION FOR DIABETES CARE WITH MEDICAL FEATURE ACTIVATION

CROSS-REFERENCE TO RELATED APPLICATIONS

This application claims the benefit of U.S. Provisional Application No. 61/816,564 filed Apr. 26, 2013. The entire disclosure of the above application is incorporated herein by reference.

FIELD

The present disclosure relates to a mobile phone application for diabetes care that allows persons with diabetes to activate and use a medical feature of the application using data received from a healthcare professional.

BACKGROUND

Persons with diabetes have difficulty regulating blood glucose levels in their bodies. As a consequence, many of these persons carry specialized electronic meters, called blood glucose meters, which allow them to periodically measure their glucose levels and take appropriate action such as administering insulin using an insulin pump. These persons may also carry with them a portable communication device, such as a mobile phone, a personal digital assistant, a tablet, or a similar mobile device. People often rely on their portable communication devices as primary means for planning, scheduling, and communicating with others. As a result, most portable communication devices are equipped with sophisticated software which provides user-friendly means for viewing and inputting data.

Persons with diabetes may wish to view and analyze results of a blood glucose measurement obtained from their glucose meter on their portable communication device. Additionally, these persons may wish to transmit the results to a healthcare professional using the portable communication device. Further, these persons may wish to receive bolus advice instruction from the healthcare professional on the portable communication device in order to manage administration of insulin. Accordingly, it is desirable to develop a diabetes management application that runs on a portable communication device and that allows persons with diabetes to transmit blood glucose measures to a healthcare professional and receive bolus advice instruction from the healthcare professional.

This section provides background information related to the present disclosure which is not necessarily prior art.

SUMMARY

In one embodiment, a method for activating a physician-prescribable feature of an application program executed on a mobile device comprises receiving, by the application program, (i) an activation code to activate a feature of the application program and (ii) one or more parameters associated with a prescription, where the activation code includes an identifier that identifies the feature to be activated. The method further comprises transmitting, by the application program, the activation code via a network from the mobile device to a server; and receiving, by the application program, an authorization code from the server, where the authorization code indicates a validity of the activation code. The method further comprises activating, by the application program, the feature using the activation code, the activation being performed in response to the activation code being valid. The method further comprises configuring, by the application program, the activated feature using at least one of the one or more parameters associated with the prescription. The method further comprises generating, using the activated feature, data based on the one or more parameters associated with the prescription.

In another embodiment, a method for activating a bolus advisor feature of an application program executed on a mobile device comprises receiving, by the application program, (i) an activation code to activate the bolus advisor feature of the application program and (ii) one or more parameters associated with a prescription, where the activation code includes an identifier that identifies the bolus advisor feature to be activated. The method further comprises transmitting, by the application program, the activation code via a network from the mobile device to a server; and receiving, by the application program, an authorization code from the server, where the authorization code indicates a validity of the activation code. The method further comprises activating, by the application program, the bolus advisor feature using the activation code, the activation being performed in response to the activation code being valid. The method further comprises configuring, by the application program, the activated bolus advisor feature using at least one of the one or more parameters associated with the prescription. The method further comprises generating, using the activated bolus advisor feature, bolus dosage data based on the one or more parameters associated with the prescription.

In yet another embodiment, a method for activating a bolus advisor feature of an application program executed on a mobile device comprises receiving, by a healthcare professional, an activation code from a server to activate the bolus advisor feature of the application program, where the activation code includes (i) a country code of a country where the activation code is to be used, (ii) an identifier that identifies the bolus advisor feature to be activated, and (iii) an alphanumeric string. The method further comprises receiving, by the application program, (i) the activation code and (ii) one or more parameters associated with a prescription from the healthcare professional; and transmitting, by the application program, the activation code via a network from the mobile device to the server. The method further comprises receiving, by the application program, an authorization code from the server, where the authorization code indicates whether the activation code is valid. The method further comprises activating, by the application program, the bolus advisor feature using the activation code, the activation being performed in response to the activation code being valid. The method further comprises configuring, by the application program, the activated bolus advisor feature using at least one of the one or more parameters associated with the prescription. The method further comprises generating, using the activated bolus advisor feature, bolus dosage data based on the one or more parameters associated with the prescription.

Further areas of applicability of the present disclosure will become apparent from the detailed description, the claims and the drawings. The detailed description and specific examples are intended for purposes of illustration only and are not intended to limit the scope of the disclosure.

DRAWINGS

FIG. 9 shows a table of parameters (settings) associated with a prescription used to setup and configure an activated feature of an application program executed on a mobile device.

Figure 1:
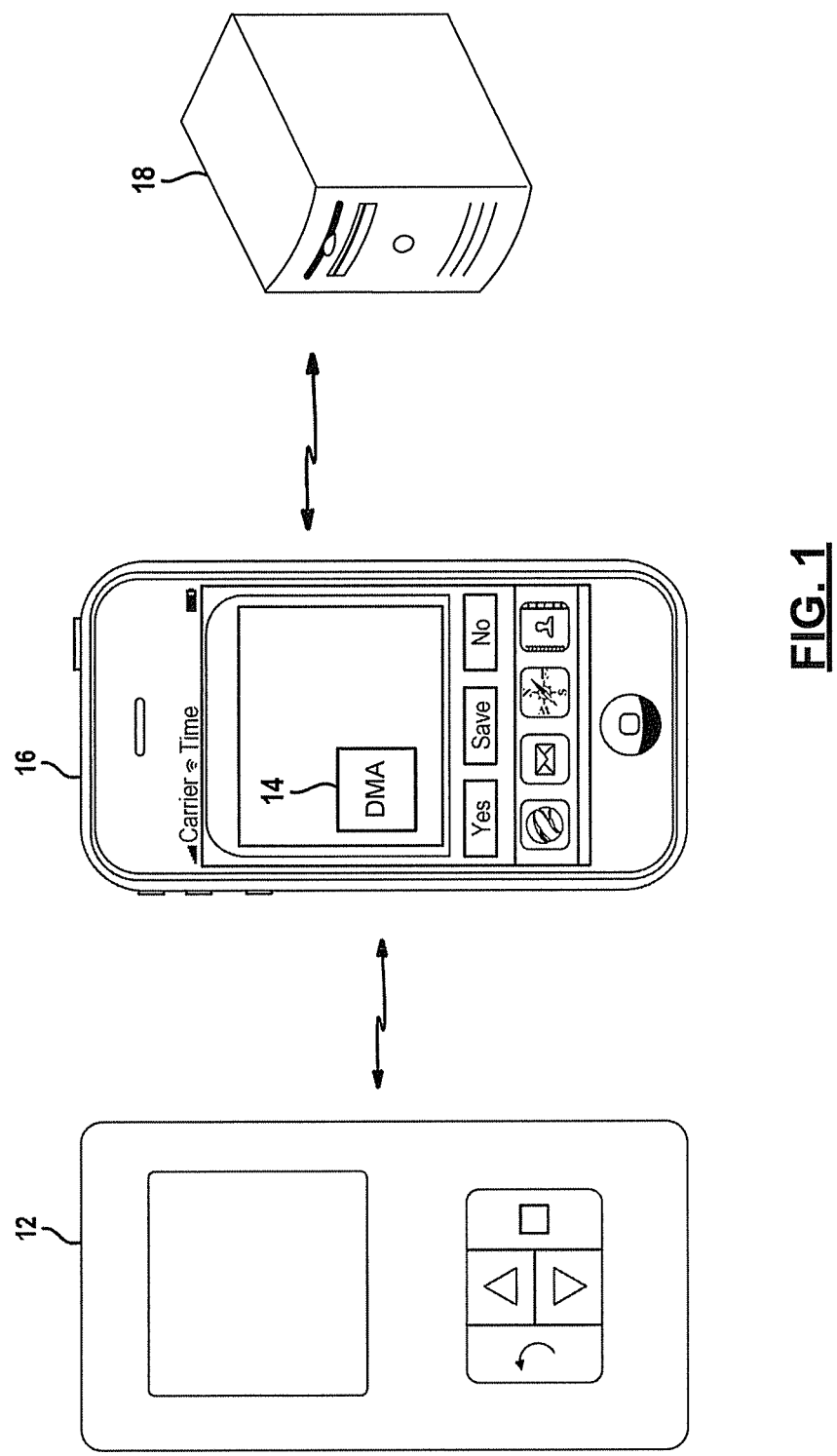
FIG. 1 is a diagram depicting a handheld glucose meter in data communication with a diabetes management application residing on a mobile phone.

The drawings described herein are, for illustrative purposes only, of selected embodiments and not all possible implementations, and are not intended to limit the scope of the present disclosure. Corresponding reference numerals indicate corresponding parts throughout the several views of the drawings.

DETAILED DESCRIPTION

FIG. 1 depicts an exemplary handheld glucose meter 12 in data communication via a wireless data link with a diabetes management application 14. The glucose meter 12 is configured to receive a sample of blood from a patient and determine a blood glucose measure for the patient from the blood sample. One or more blood glucose measures may in turn be transmitted over the wireless data link to the diabetes management application 14 for further processing. In an exemplary embodiment, the diabetes management application 14 resides on a mobile phone 16. In other embodiments, the diabetes management application 14 may be native to a remote server 18 with its user interface presented on the mobile phone 16.

The mobile phone 16 may be a handheld computing device arranged to include a hardware layer, an operating system layer, an application layer, and a user interface layer. For example, the hardware layer includes a processor and memory. The operating system layer includes an operating system. The operating system is a set of instructions stored in memory and executed by the processor. For example only, the operating system may include Android OS, iOS, or any other suitable mobile phone or tablet operating system. The application layer includes at least one software application, for example the diabetes management application 14. The user interface layer includes a user input device, such as a keyboard or a touch screen interface, and a display screen.

In some embodiments, data is transferred to and from the glucose meter 12 using the Bluetooth wireless technology standard (e.g., low energy feature of Bluetooth 4.0) although other types of communication transports are contemplated by this disclosure. For example only, data may be transferred to and from the glucose meter 12 using a WiFi network connection or a physical cable connection. In some embodiments, the glucose meter 12 is physically connected to a personal computer (PC). The glucose meter 12 transfers data over the physical connection and is stored in memory within the PC. The PC may be configured to transmit data received from the glucose meter 12 to another computing device, such as the mobile phone 16. In another embodiment, the PC may be configured to transmit data received from the glucose meter 12 to the remote server 18. The mobile phone 16 may then communicate with the remote server 18. For example, the remote server 18 may transmit data to the mobile phone 16. The mobile phone 16 stores the received data. The diabetes management application 14 may process the data stored within the mobile phone 16.

In other embodiments, the mobile phone 16 may communicate the one or more glucose measures to the remote server 18. For example, the mobile phone 16 may be configured to determine whether to communicate the one or more glucose measures to the remote server 18. Upon receiving the one or more glucose measures from the meter 12, the mobile phone 16 determines whether to communicate the one or more glucose measures to the remote server 18. In some embodiments, the mobile phone 16 is configured to automatically communicate the one or more glucose measures to the remote server 18.

In yet another embodiment, the mobile phone 16 is configured to determine whether the remote server 18 has sent a glucose measure request to the mobile phone 16. When the mobile phone 16 determines the remote server 18 has sent a glucose measure request to the mobile phone 16, the mobile phone 16 communicates the one or more glucose measures to the remote server 18. The glucose measure request may be a signal communicated over a wireless network to the mobile phone 16.

The remote server 18 stores the one or more glucose measures in memory within the remote server 18. The remote server 18 may perform further processing on the one or more glucose measures. For example, the remote server 18 associates the one or more glucose measures with other data relevant to the patient such as patient name, patient age, the date and time the one or more glucose measures were collected, patient measurement history, and any other relevant data. The remote server 18 is configured to allow remote access to data stored within the remote server 18. For example, a physician of the patient may access the one or more glucose measures stored on the remote server 18 in order to treat the patient. It is understood that while only the one or more glucose measures is discussed, the principles described herein also apply to any patient data received by the glucose meter 12.

In some embodiments, the diabetes management application 14 includes a bolus calculator. For example, the diabetes management application 14 may receive the one or more glucose measures from the glucose meter 12. The diabetes management application 14 determines a bolus calculation based on the one or more glucose measures. Further discussions of the bolus calculator can be found in the commonly assigned U.S. patent application Ser. No. 13/593,593, filed Aug. 24, 2012, the entire disclosure of which is hereby incorporated by reference.

Figure 2:
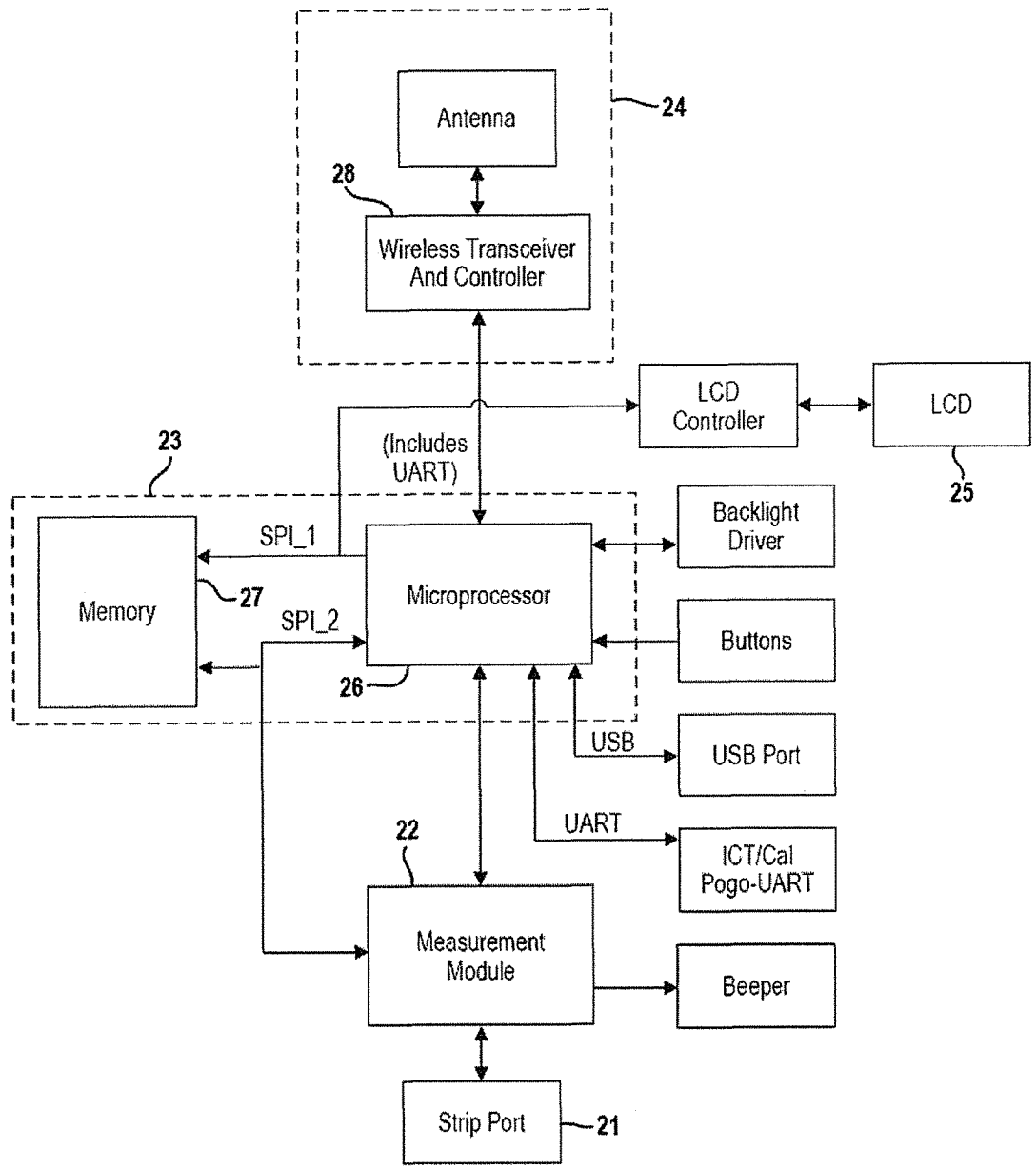
FIG. 2 is a block diagram of an exemplary hardware arrangement for the glucose meter.

FIG. 2 depicts an exemplary hardware arrangement for the glucose meter 12. The glucose meter 12 is comprised generally of a measurement module 22, a processing subsystem 23, and a communication subsystem 24. Each of these components is further described below. While the primary components are discussed herein, it is understood that other components (e.g., batteries) may be needed for the overall operation of the meter 12.

The measurement module 22 cooperatively interacts with a test strip inserted into a strip port 21 to determine a glucose measure from the sample of blood on the test strip. The measurement module 22 may include calibration information for the test strips being read by the meter 12. As used herein, the term module may refer to, be part of, or include an application Specific Integrated Circuit (ASIC); an electronic circuit; a combinational logic circuit; a field programmable gate array (FPGA); a processor (shared, dedicated, or group) that executes code; other suitable components that provide the described functionality; or a combination of some or all of the above. The term module may further include memory that stores code executed by the processor, where code, as used above, may include software, firmware, and/or microcode, and may refer to programs, routines, functions, classes, and/or objects.

The processing subsystem 23 is configured to receive the glucose measures from the measurement module 22 which may in turn be stored in memory by the processing subsystem 23. Glucose measures may also be displayed by the processing subsystem 23 on a display 25. The user can interact with the meter 12 using various user interface components, such as buttons, switches, a speaker, a microphone, a USB port, etc. Each of these components is interfaced with the processing subsystem 23. In an exemplary embodiment, the processing subsystem 23 includes a microprocessor 26 and one or more volatile and/or non-volatile memories 27 although other implementations are envisioned for the processing subsystem 23.

The processing subsystem 23 is also interfaced with the communication subsystem 24. In an exemplary embodiment, the communication subsystem 24 includes a wireless transceiver 28. The wireless transceiver 28 operates to communicate the glucose measures and other data wirelessly via a data link to a remote device physically separated from the meter 12. The communication subsystem 24 can also include an antenna, a microcontroller, voltage and power control circuits, and a flash memory device. Although a few primary components of the meter 12 are discussed herein, it is readily understood that other components (e.g., power source) may be needed to implement the meter 12.

Figure 3:
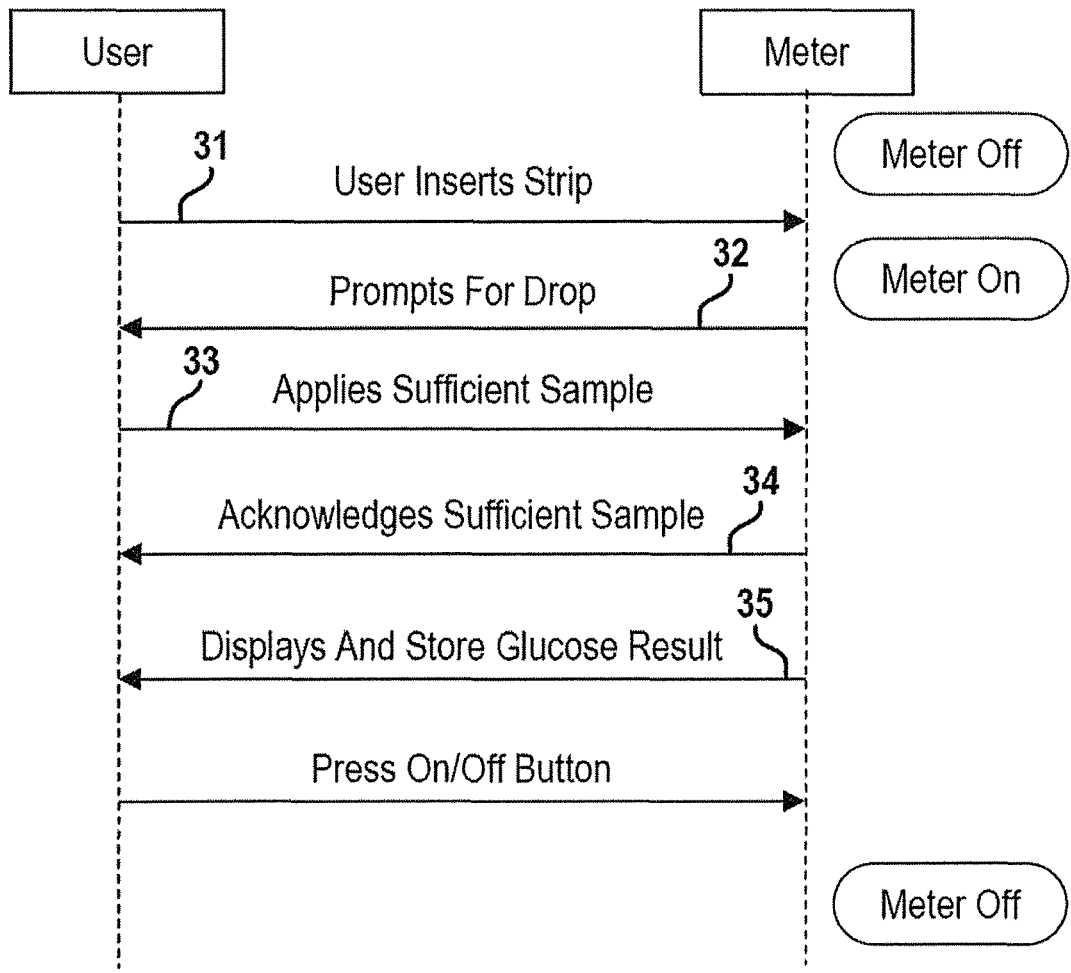
FIG. 3 is a sequence diagram illustrating an exemplary sequence for taking a blood glucose measure using the glucose meter.

FIG. 3 depicts an exemplary sequence for taking a blood glucose measure using the blood glucose meter 12. The user may insert a test strip at 31 into a port of the glucose meter 12. Insertion of the test strip prompts the glucose meter 12 to power on. The user may alternatively power on the glucose meter 12 using an on/off button. In this case, the glucose meter 12 will prompt the user to insert a test strip. The user may also power on the glucose meter 12 without inserting a test strip into the meter. In any of these cases, the glucose meter 12 may perform a quality check on the test strip inserted into the meter 12. Once the quality check has been completed, the meter 12 is ready to perform a test.

To begin a test, the user is prompted at 32 for a sample of blood. In response to the prompt, the user provides a blood sample at 33 using the test strip, where the test strip includes a reaction site that receives the blood sample from the patient. Upon receipt of the blood sample, the glucose meter 12 will proceed to analyze the blood sample in a manner readily known in the art. Before doing so, the glucose meter 12 may acknowledge the sufficiency of the blood as indicated at 34.

During the analysis, a blood glucose measure is obtained from the blood sample. The blood glucose measure will be displayed to the user and stored on the glucose meter 12 as indicated at 35. Stored glucose measures may be uploaded subsequently from the glucose meter 12 in a batch manner to a physician's computer.

Figure 4:
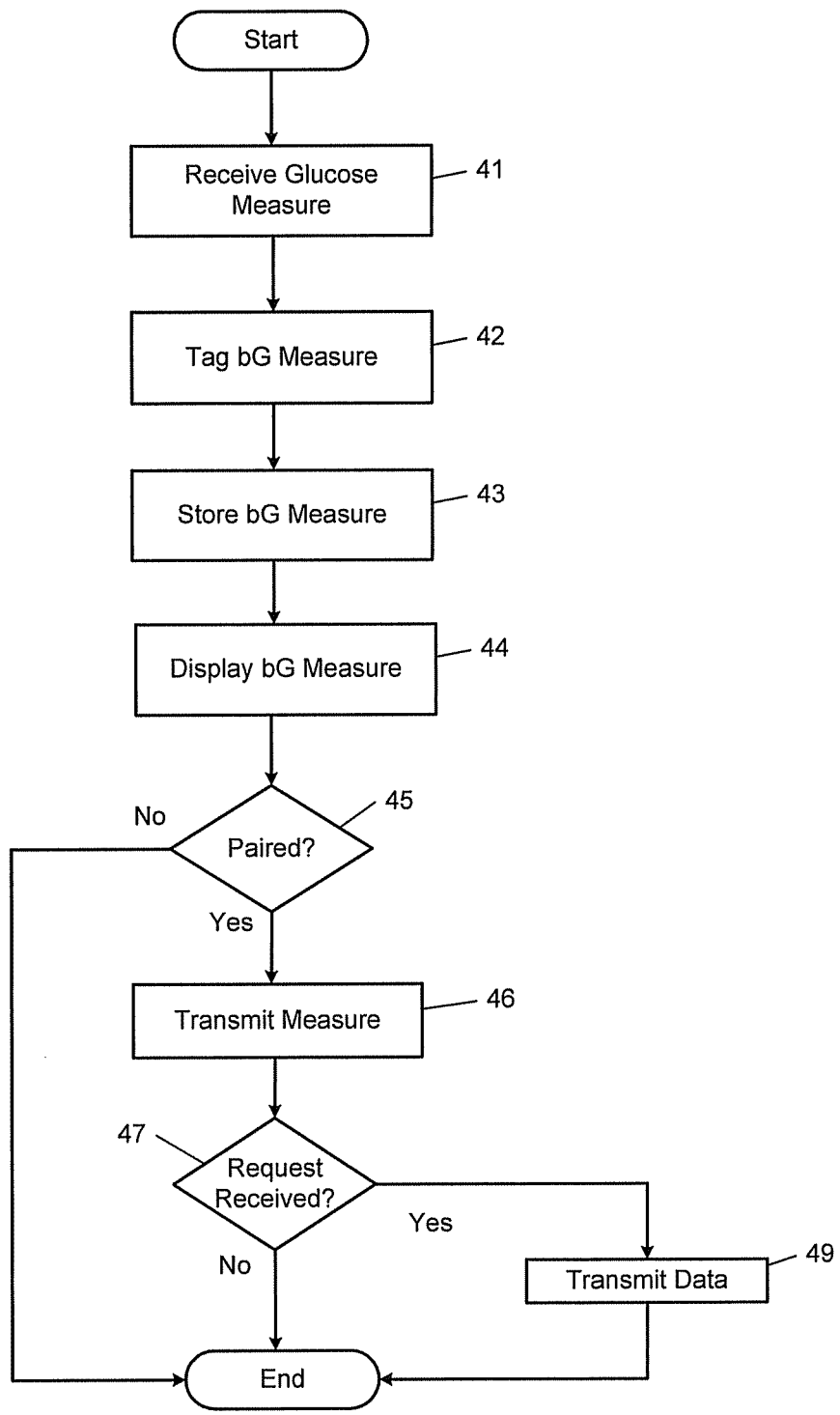
FIG. 4 is a flowchart illustrating an exemplary technique for transmitting blood glucose measures individually from the glucose meter.

FIG. 4 shows that rather than sending blood glucose measures in a batch manner, the glucose meter 12 may be configured to transmit blood glucose measures individually. The blood glucose measures may be transmitted, for example to a mobile phone, such as the mobile phone 16, or some other portable computing device carried by the user. Because the mobile phone 16 is typically in close proximity to the user, it may be used as a data collector for the patient's blood glucose measures. The diabetes management application 14 residing on the mobile phone 16 can then be used for data analysis as well as other sophisticated diabetes management functions. Consequently, the processing power and memory available on the glucose meter 12 can be streamlined, thereby reducing the cost of the glucose meter 12.

Upon determining a blood glucose measure, the blood glucose measure is first tagged at 42 with identifying information. Identifying information may include but is not limited to a timestamp for when the measure was taken, a serial number for the meter 12, and other information pertaining to the test strip. Each blood glucose measure is also tagged with a unique sequence number assigned by the glucose meter 12. In one embodiment, a counter is incremented each time a glucose measure is taken and the value of the counter is assigned to the blood glucose measure. The sequence number may be used to retrieve missing data from the glucose meter 12 as is further described below. Once tagged, the blood glucose measure is stored at 43 in a memory of the glucose meter 12 and displayed to the user at 44 on a display of the glucose meter 12.

Next, the glucose meter 12 determines at 45 whether it is paired via a wireless data link with another device, such as the mobile phone 16. The current blood glucose measure is transmitted at 46 to the mobile phone 16 when the glucose meter 12 is paired to the mobile phone 16. The glucose meter 12 may be configured to automatically transmit the blood glucose measure to the mobile phone 16. Alternatively, the person with diabetes may operate the glucose meter 12 manually to transmit the blood glucose measure to the mobile phone 16. While reference is made throughout this disclosure to a message being sent with a single glucose measure, it is envisioned that in some embodiments the message transmitted by the glucose meter 12 can contain one or more glucose measures.

In one embodiment, the blood glucose measure is transmitted automatically and without user intervention. For example, after taking a glucose measure, the glucose measure is transmitted automatically after a predefined timeout period (e.g., five seconds) without receiving any input from the user. In another embodiment, the blood glucose measure is transmitted automatically in response to the user navigating away from the measurement result screen. In a similar manner, the blood glucose measure may be transmitted automatically in response to the meter 12 being powered down by the user. It is envisioned that the mobile phone 16 and/or the diabetes management application 14 is authenticated with the glucose meter 12 during the pairing process.

The glucose meter 12 may also receive a request for missing glucose measures at 47 from the diabetes management application 14. In one embodiment, the request identifies any missing glucose measures by its sequence number as will be further described below. In response to receiving a request, the glucose meter 12 will transmit the missing glucose measures at 49 to the diabetes management application 14. It is to be understood that only the relevant steps are discussed in relation to FIG. 4 and that other software-implemented instructions may be needed to transmit data from the glucose meter 12. In an exemplary embodiment, the method described above is implemented by a user interface module residing on the glucose meter 12.

Figure 5:
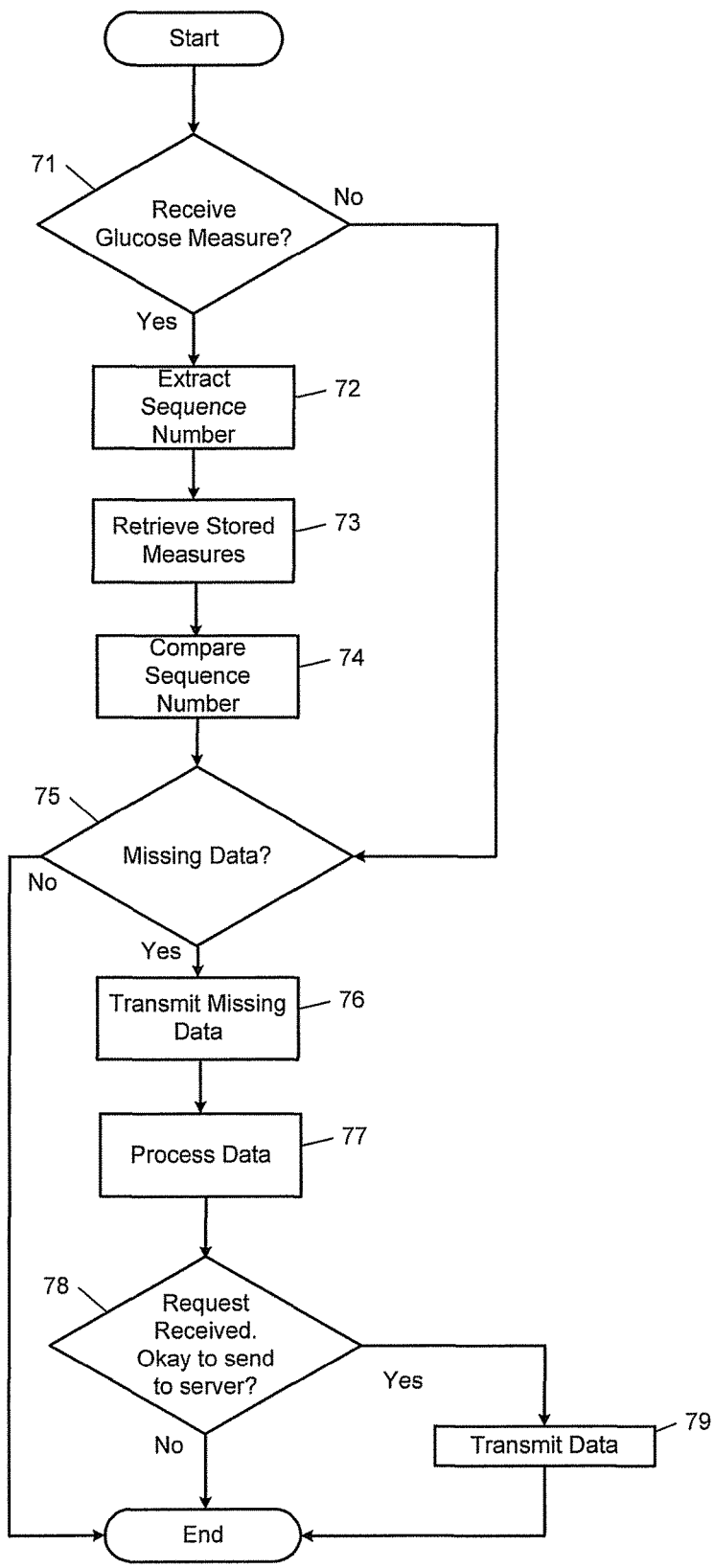
FIG. 5 is a flowchart illustrating an exemplary technique for processing glucose measures received by the diabetes management application.

FIG. 5 depicts an exemplary method for processing glucose measures received by the diabetes management application 14 residing on the mobile phone 16. In the exemplary embodiment, glucose measures are transmitted individually to the diabetes management application 14 as described in relation to FIG. 4. It is envisioned that other techniques for transmitting the glucose measure to the diabetes management application 14 are contemplated by this disclosure. For example, the glucose meter 12 may transmit the glucose measures via a WiFi connection, a Bluetooth connection, a cable connection, or any other suitable data transfer connections and/or protocols.

Upon receiving a glucose measure at 71, a sequence number associated with the glucose measure is first determined by the diabetes management application 14. A unique sequence number is assigned by the glucose meter 12 to each glucose measure as described above. Thus, the sequence number associated with the glucose measure can be extracted at 72 from the data packet or message received from the glucose meter 12. In some embodiments, a series of glucose measures previously received from the glucose meter 12, along with their associated sequence numbers, may be stored in a memory device and thus be accessible to the diabetes management application 14. In other embodiments, only the most recently received glucose measure and its sequence number is stored by the diabetes management application 14. In either case, the stored glucose measure(s) along with associated sequence number(s) are retrieved from memory.

A comparison is made at 74 between the sequence number extracted from the present glucose measure and the sequence numbers of the stored glucose measures. A request for missing glucose measures is transmitted by the diabetes management application 14 to the glucose meter 12 at 76 when an omission in the sequence is detected. For example, a request for missing glucose measures is transmitted when the extracted sequence number is 84 and the highest stored sequence number is either 81 or 82. Conversely, a request is not transmitted when the extracted sequence number is 84 and the highest stored sequence number is 83. Because this comparison is made for each glucose measure received by the diabetes management application 14, a comparison of the extracted sequence number only needs to be made to the highest stored sequence number. In other embodiments, the diabetes management application 14 may analyze the series of glucose measures for omitted measures and send a request for each glucose measure missing from the series of glucose measures. The request for missing glucose measures can be transmitted in accordance with the protocol described in relation to FIG. 1.

At 77 the diabetes management application 14 processes the glucose measures. For example, the diabetes management application may correlate the most recently received glucose measure with previously received glucose measures. The diabetes management application 14 may then generate a graphical representation of the glucose measures. The diabetes management application 14 displays the graphical representation on a screen of the mobile phone 16. The diabetes management application 14 may receive a request to transmit the glucose measure(s) to a remote location, such as the remote server 18.

At 78 the diabetes management application 14 determines whether a request was received to transmit the glucose measure(s) to the remote server 18. When the diabetes management application 14 determines that a request was received, the diabetes management application 14 transmits the glucose measure(s) to the remote server 18. Transmitting the glucose measure(s) may include packaging the glucose measure(s) in a packet configured to be received and interpreted by the remote server 18 at 79. In another embodiment, the diabetes management application 14 automatically transmits the glucose measure(s) to the remote server 16 upon receiving the glucose measure(s) from the meter 12.

Figure 6:
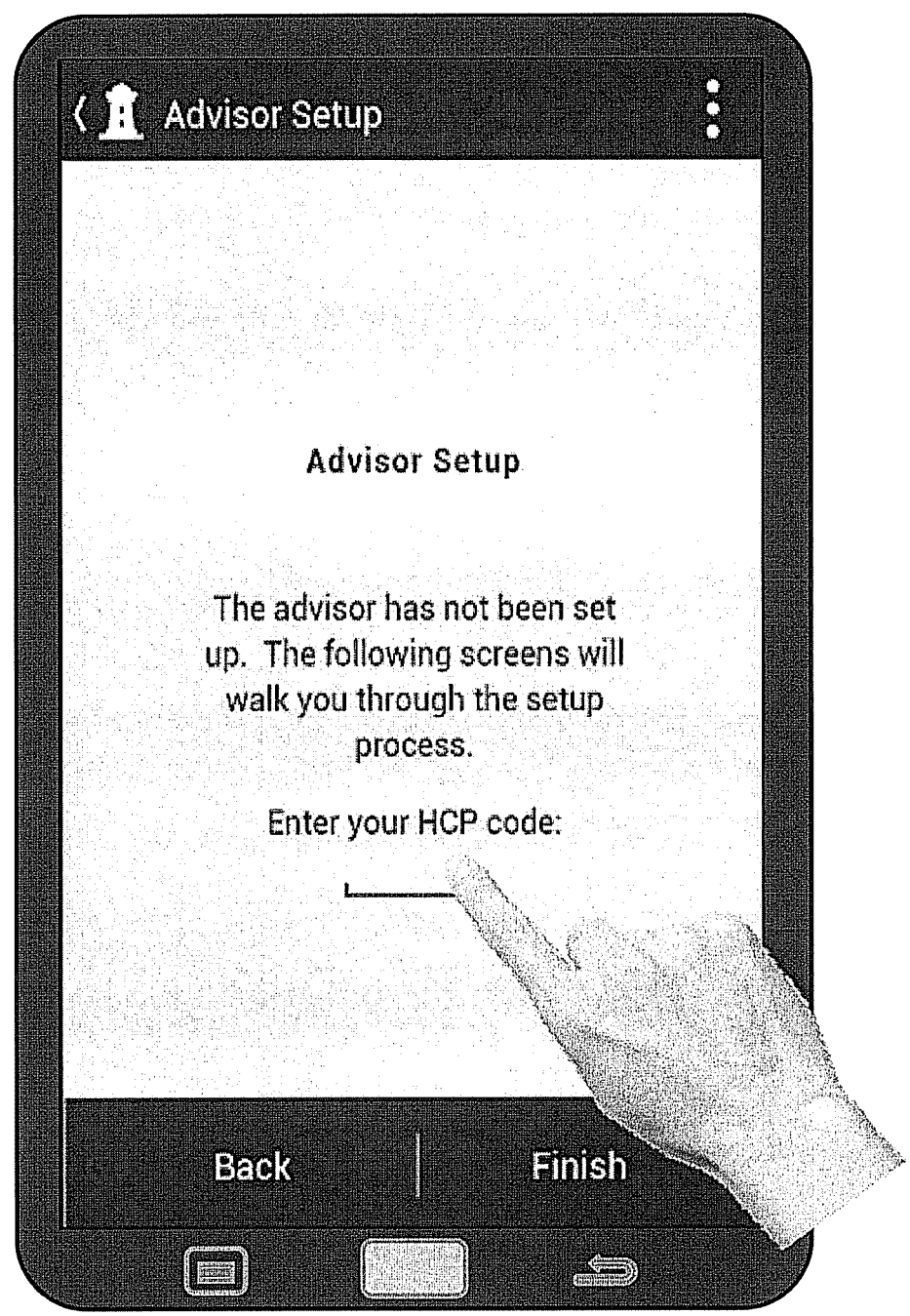
FIG. 6 shows a screenshot of a mobile phone application for diabetes care including a bolus advisor.

FIG. 6 shows a screenshot of the diabetes management application 14 according to the present disclosure including a bolus advisor that is downloaded on the mobile phone 16 as part of the application but not activated due to medical safety concerns. To address the medical safety concerns, the person with diabetes must receive guidance from a healthcare professional prior to receiving an activation code to activate the bolus advisor. The person with diabetes enters the activation code received from the healthcare professional into the application to gain access to the bolus advisor. The activation key concept disclosed herein with reference to the bolus advisor feature of the application can also be applied to other medical features of the application such as a carbohydrate counter and insulin pump control, for example.

To obtain the activation key, the person with diabetes may send an email message or SMS to a healthcare professional using the mobile phone 16. The email message or the SMS may include information specific to the mobile phone 16. The information specific to the mobile phone may be used to generate an activation key specifically for the mobile phone 16. Alternatively, the healthcare professional may provide the activation key to the person with diabetes in person.

The healthcare professional may have an application that generates the activation key with constraints such as a time limitation for using the activation key that is provided to the person with diabetes. The person with diabetes uses the activation key to activate the bolus advisor and then enters a bolus advice parameter provided by the healthcare professional into the diabetes management application 14. The diabetes management application 14 then calculates bolus. Based on the calculated bolus, an insulin pump, which communicates with the mobile phone 16 via the diabetes management application 14, administers insulin to the person with diabetes.

Typically, bolus calculators require a prescription. Use of a written prescription, however, may create an administrative burden to the healthcare professional and may inconvenience the person with diabetes since such a requirement would erode the usefulness and flexibility offered by the diabetes management application 14, which is typically downloaded from an app store to the mobile phone 16. Instead, the healthcare professional transmits to the person with diabetes an activation key to activate the bolus advice feature and the necessary parameters for the bolus advice feature. The person with diabetes enters the bolus activation key into the diabetes management application 14 on the mobile phone 14 and then accesses the bolus advice feature of the diabetes management application 14.

The person with diabetes can activate the bolus advice feature of the diabetes management application 14 using a simple setup provided by the diabetes management application 14. The setup may include inputting information such as bG target range, meal rise, insulin to carbs ratio, insulin to bG (sensitivity) ratio, and maximum bolus. Other parameters may use default values. The diabetes management application 14 may use two separate screens to allow the person with diabetes to enter the activation code and to input the information into the simple setup. The diabetes management application 14 can enable or disable the need for the activation key to activate the bolus advisor feature to meet the needs of various countries.

The diabetes management application 14 may run on a variety of mobile devices such as Android-based phone, iPhones, and/or Windows phones. The diabetes management application 14 can run on smartphones, tablets, as well as other portable computing devices. The diabetes management application 14 can support core functionality (data entry, reminders, structured tests, and simple reporting) when disconnected from the cellular network and the Internet. When network access is available, the diabetes management application 14 can allow data sharing with healthcare professionals and caregivers via the mobile device communication system or a web account data sharing system. The diabetes management application 14 can also support connectivity to a Bluetooth Low Energy (BLE) bG Meter and other bG meters via BLE/BT transport.

The purpose of the diabetes management application 14 is to make it easier for patients to provide reliable health information to their caregivers and healthcare professionals for the purpose of helping the patient improve their ability to manage their diabetes. The diabetes management application 14 is intended for use by individual persons with diabetes. The diabetes management application 14 can support entry, transfer, storage, display, and analysis of blood glucose data and other related health indicators. As people generally have their mobile devices with them all the time, the diabetes management application 14 application can provide persons with diabetes an always-available and easy-to-use way to log and share their health information.

The diabetes management application 14 can support data sharing by means of SMS and MMS messages, by email delivery of reports, and by data upload to a web-based diabetes management system. These options can make patient data available to the patient's caregivers and healthcare professionals, improving their ability to help the patient manage their diabetes.

The diabetes management application 14 can support a plurality of languages. The diabetes management application 14 can support additional structured test protocols, integration of a food database, and transfer of data from other BT/BLE-enabled health devices such as blood pressure cuffs, weight scales, and so on.

While the code of the diabetes management application 14 may differ to the extent that it can support different mobile devices running different operating systems, the diabetes management application 14 provides a common platform for diabetes management in at least the following senses: The diabetes management application 14 allows easy addition of new languages, includes clean separation of core logic from user interface functions, includes clean separation of core logic from data access mechanisms, and supports addition of new features.

The user interface of the diabetes management application 14 can be delivered both by the diabetes management application 14 and by content hosted on a web-based diabetes management system. The diabetes management application 14 can include external system interfaces to: export and import of data and settings from the web-based diabetes management system; receive data from supported BT/BLE Meter; email, MMS, and SMS text messaging (when available); backup and restore data from via email; export XML file to the web-based diabetes management system; and 3rd party data analytics service.

Figure 7:
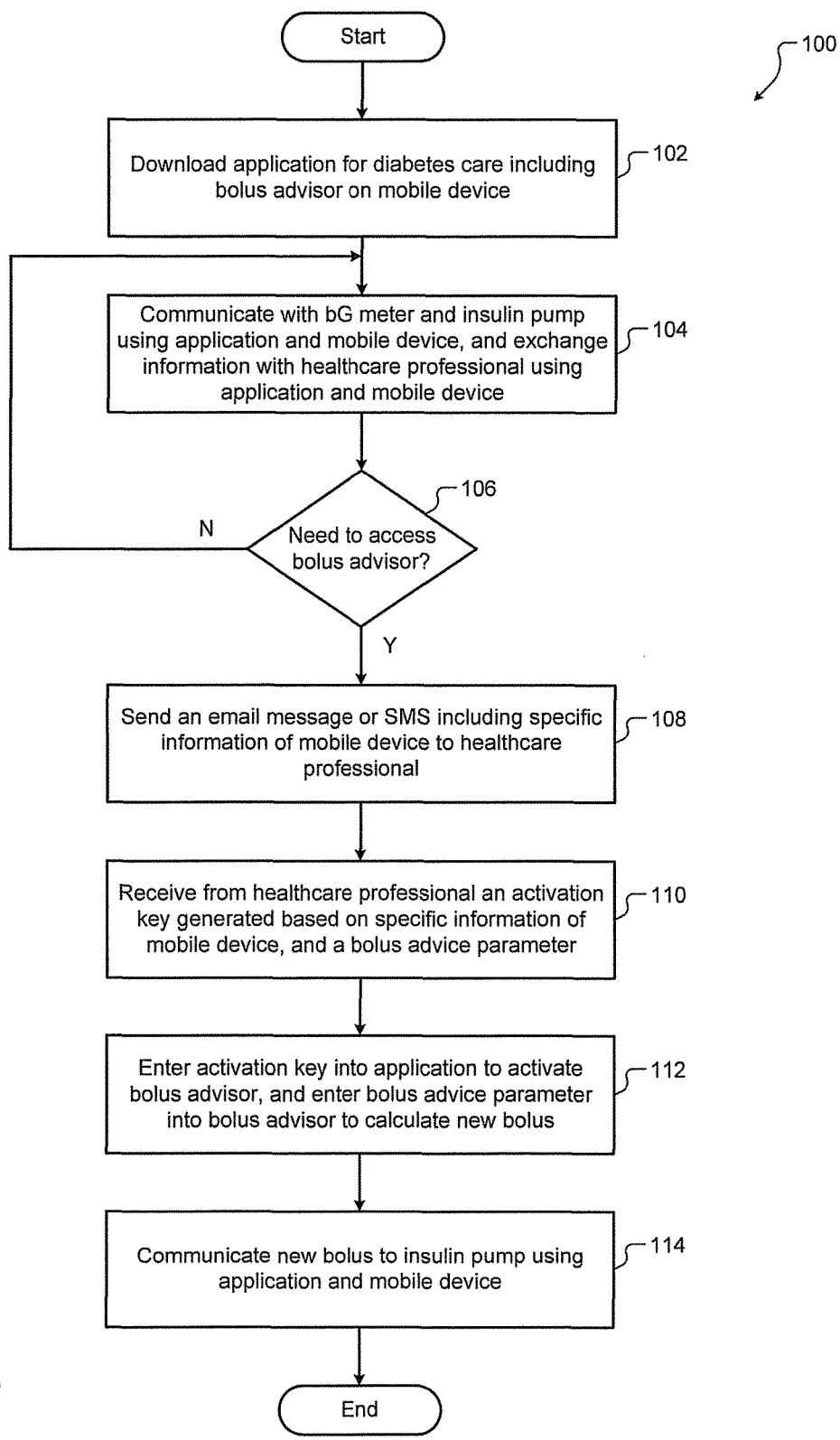
FIG. 7 is a flowchart illustrating an exemplary technique for activating a bolus advisor on a mobile phone application for diabetes care.

FIG. 7 is a flowchart illustrating an exemplary technique for activating a bolus advisor feature on a mobile phone application for diabetes care. At 102, the person with diabetes downloads an application such as the diabetes management application 14 on a mobile device such as the mobile phone 16. The application includes among other things a bolus advisor. In addition, the application may include other medical features such as a carbohydrate counter and insulin pump control. The teachings of the present disclosure, while disclosed with reference to the bolus advisor feature, can also be applied to other medical features such as the carbohydrate counter, the insulin pump control, and so on.

At 104, the person with diabetes may communicate with a blood glucose meter and/or an insulin pump using the application and the mobile device. For example, the person with diabetes may perform a blood glucose test using the blood glucose meter and may gather data related to the blood glucose test from the blood glucose meter using the application and the mobile device. In addition, the person with diabetes may control and/or test the blood glucose meter and/or the insulin pump using the application and the mobile device.

At 106, the person with diabetes may decide whether to access the bolus advisor in the application. If accessing the bolus advisor is unnecessary, the person with diabetes may continue to use the application and the mobile device to communicate with the blood glucose meter and/or the insulin pump as described above. In addition, the person with diabetes may continue to use the application and the mobile device to communicate with the healthcare professional. If, however, the person with diabetes needs to access the bolus advisor in the application, the person with diabetes may send an email message or SMS to a healthcare professional at 108. The email message or the SMS may include specific information of the mobile device. For example, the specific information of the mobile device may include but is not limited to a serial number of the mobile device, an identifier associated with a processor (e.g., CPU ID), or an identifier associated with a communication device (e.g., a MAC address), and so on. In addition, the email message or the SMS may include data gathered by the application and the mobile device from the blood glucose meter and/or the insulin pump.

At 110, the person with diabetes may receive from the healthcare professional an email message or SMS that includes an activation key generated by the healthcare professional based on the specific information of the mobile device. In addition, the email message or SMS may include a bolus advice parameter generated by the healthcare professional based on the data from the blood glucose meter sent by the person with diabetes. For example, the bolus advice parameter may include but is not limited to one or more of bG target range, meal rise, insulin to carbs ratio, insulin to bG (sensitivity) ratio, and maximum bolus. The email message or SMS may also include diagnostic and/or calibration information for the blood glucose meter and/or the insulin pump.

At 112, the person with diabetes may enter the activation key into the application to activate the bolus advisor. In addition, the person with diabetes may enter the bolus advice parameter into the bolus advisor feature of the application to calculate new bolus. At 114, the application in the mobile device may communicate the new bolus to the insulin pump using the mobile device. Subsequently, the insulin pump may administer the new bolus to the person with diabetes.

In some implementations, the healthcare professional may include the bolus advice parameter in the activation key itself so that the person with diabetes has to enter only the activation key into the application, and on entering the activation key, the bolus advisor automatically configures itself based on the bolus advice parameter included in the activation key. This can ensure that the person with diabetes cannot alter the bolus advice parameter. Additionally, each time the bolus advice needs to be changed, the person with diabetes will be required to request and acquire a new activation key. The bolus advice parameter and the bolus calculated based on the bolus advice parameter will remain valid and in effect for the duration for which the activation key remains valid or until a new activation key is obtained, whichever occurs first.

In some implementations, the application may verify whether the activation key received is in fact from a trusted source. For example, the verification may be performed using a hashing algorithm included in the application. The healthcare professional may encrypt the activation key using the same hashing algorithm used by the application. For example, the activation key may be generated by hashing identifying information (e.g., name, patient ID, and so on) of the person with diabetes, an identifier associated with the mobile device received via email or SMS message from the person with diabetes, etc.

The application uses the hashing algorithm to decrypt the activation key when entered by the person with diabetes. The hashing algorithm in the application compares the decryption result to the identifying information entered into the application by the person with diabetes and/or the identifier associated with the mobile device. If the decryption result matches the identifying information of the person with diabetes and/or the identifier associated with the mobile device, the application determines that the activation key is received from a trusted source, and the application grants access to the bolus advisor. If the decryption result does not match the identifying information of the person with diabetes and/or the identifier associated with the mobile device, the application determines that the activation key is not received from a trusted source, and the application does not grant access to the bolus advisor.

Figure 8:
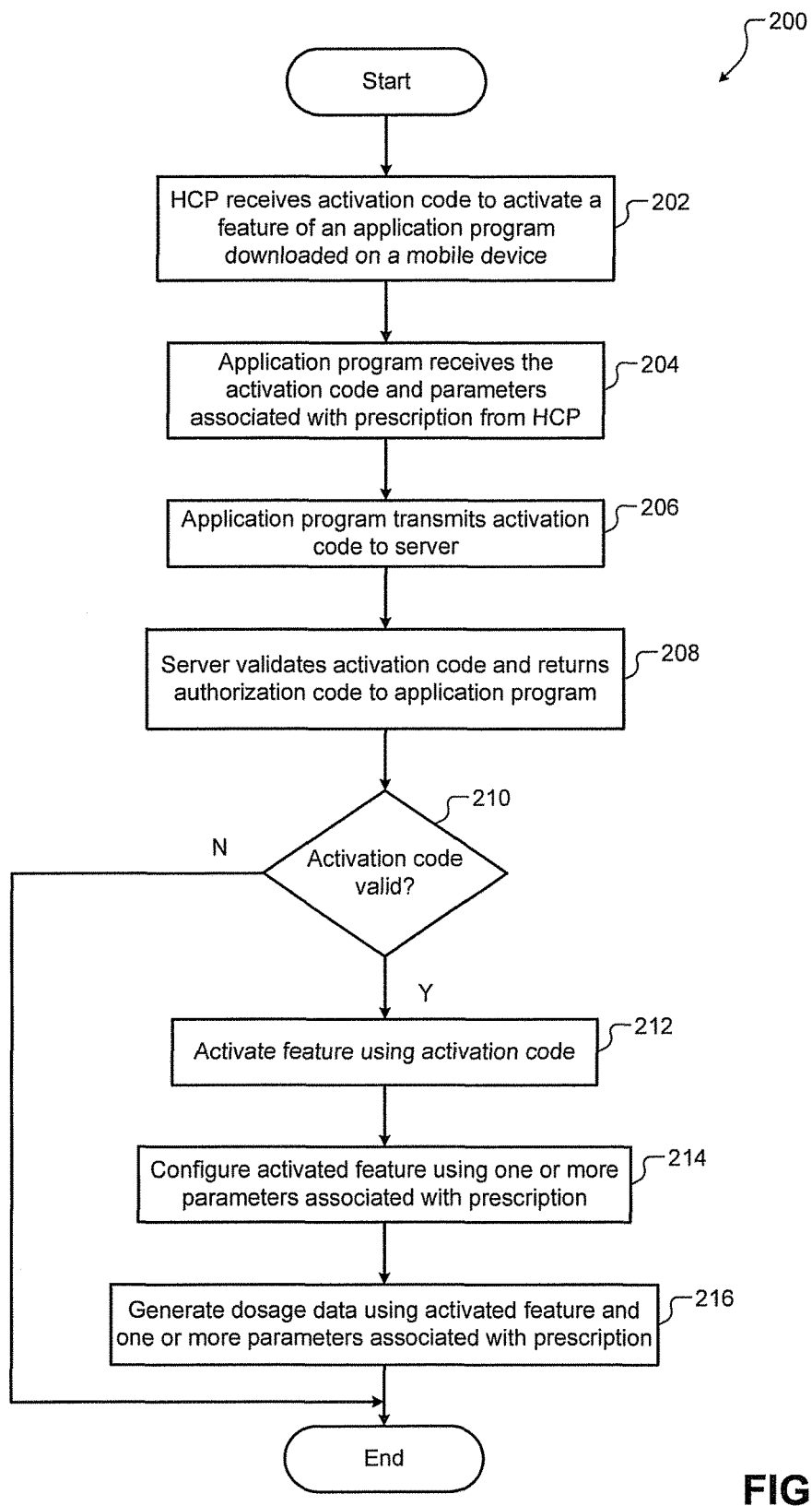
FIG. 8 is a flowchart of a method for activating a physician-prescribable feature of an application program executed on a mobile device.

FIG. 8 is a flowchart of a method 200 for activating a physician-prescribable feature of an application program executed on a mobile device. The application program is downloaded by a patient (e.g., a person with diabetes) on the mobile device. The application program includes one or more features that require a prescription from a healthcare professional (e.g., a physician) to activate and use the feature. For example, the feature may include a bolus advisor feature.

At 202, the physician may obtain an activation code to activate the feature. For example, the physician may log into a server that generates and distributes activation codes. The physician may request an activation code to activate a feature of the application program used by a patient. The server may verify the credentials of the physician and provide the activation code to the physician. For example, the server may provide the activation code in a printed form or electronically (e.g., via an email).

Each activation code may be unique (i.e., different) and may not be repeated. Each activation code may include an identifier that identifies the feature to be activated, a country code of the country where the activation code is to be used, and an alphanumeric string. For example, the identifier may include one numeral, the country code may include two characters, and the alphanumeric string may include four characters. The activation code may have an expiration date. For example, if the prescribing physician requires the person with diabetes to return in six months to evaluate and modify the bolus advice parameters, the activation could have a time limit where it stops working after the set time. In other words, the activation code can remain valid for a predetermined time period and can expire at an end of the predetermined time period.

The physician may then provide the activation code and one or more parameters associated with the prescription to the patient (e.g., via an SMS, an email, or a telephone call). The parameters are used to control treatment of the patient through the feature of the application program and are therefore prescribed by the physician. Some of the parameters may be paired (i.e., tied) to the activation code and may be used to setup the feature once activated. Other parameters may be used by the feature subsequent to the activation and setup procedure to generate dosage data.

For example, FIG. 9 shows a table that includes settings (i.e., parameters) that the physician may be required to prescribe to a patient with diabetes. The parameters listed under Basic Settings are used in the basic setup of the bolus advisor feature of the application program. These parameters may be paired (i.e., tied) to the activation code, for example. The parameters listed under Additional Settings can be adjusted using a Settings/Advisor menu of the feature or the application program.

At 204, the application program receives the activation code and one or more parameters associated with the prescription from the physician. At 206, the application program transmits the activation code from the mobile device to the server via a network for validation. At 208, the server may verify one or more of the following in order to determine whether the activation code is valid. For example, the server may verify whether the activation code is received from the application program authorized to use the activation code and not from any other unauthorized application program. The server may verify whether the activation code is to be used in the country where the application program is being used. The server may verify whether the activation code has been used before. The server may verify whether the activation code has been disabled or deleted as a result of being lost or stolen.

If one or more of the above is verified, the server may determine that the activation code is valid and generate an authorization code. The authorization code may include the country code indicating the country in which the activation code is to be used, the identifier that identifies the feature to be activated using the activation code, the activation code, a status indicator indicating whether the activation code is valid, and a time stamp indicating the date and time when the activation code is validated.

In some implementations, the authorization code may include the activation code, a time stamp including the date and time when the activation code is validated, the identifier of the feature to be activated using the activation code, and an authorization indicating that the activation code is valid. The authorization may include an encrypted string obtained by concatenating the time stamp, the identifier, and the country code, followed by performing hashing and encryption functions. Additional or other security mechanisms may be used to ensure security and integrity of the activation code. The server may return the authorization code to the application program via the network.

At 210, the application program checks whether the authorization code received from the server indicates that the activation code is valid. At 212, if the authorization code indicates that the activation code is valid, the application program activates the feature using the activation code. At 214, the application program uses some of the parameters associated with the activation code, which are received with the activation code from the physician, to perform an initial setup or configuration of the activated feature. At 216, the activated feature generates dosage data according to the prescription using other parameters received with the activation code from the physician.

Following are examples of parameters that may be tied to the activation code and that may be used to perform an initial setup or configuration of the bolus advisor feature: a target range, which includes acceptable upper and lower blood glucose levels when fasting or before a meal; meal rise, which accommodates an expected rise in blood glucose levels in response to food intake; a carb ratio, which is an amount of insulin necessary to account for a specified amount of carbohydrates; an insulin sensitivity, which is an amount of insulin necessary to lower blood glucose levels by a specified amount; and a maximum bolus, which is a maximum amount of insulin to be delivered at one time.

Following are examples of additional parameters that may be used to generate bolus dosage data: a snack size, which defines a threshold of carbohydrates above which a meal rise is triggered; an offset time, which is a length of time after a bolus is administered until a reduction in blood glucose levels begins; an acting time, which is a length of time insulin is expected to be effective at lowering blood glucose levels; insulin increment, which a unit or a fraction of a unit of insulin; and hypo, which is a setting below which blood glucose levels are considered hypoglycemic.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

The techniques described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

Some portions of the above description present the techniques described herein in terms of algorithms and symbolic representations of operations on information. These algorithmic descriptions and representations are the means used by those skilled in the data processing arts to most effectively convey the substance of their work to others skilled in the art. These operations, while described functionally or logically, are understood to be implemented by computer programs. Furthermore, it has also proven convenient, at times to refer to these arrangements of operations as modules or by functional names, without loss of generality.

Unless specifically stated otherwise as apparent from the above discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

Certain aspects of the described techniques include process steps and instructions described herein in the form of an algorithm. It should be noted that the described process steps and instructions could be embodied in software, firmware or hardware, and when embodied in software, could be downloaded to reside on and be operated from different platforms used by real time network operating systems.

The present disclosure also relates to an apparatus for performing the operations herein. This apparatus may be specially constructed for the required purposes, or it may comprise a general-purpose computer selectively activated or reconfigured by a computer program stored on a computer readable medium that can be accessed by the computer. Such a computer program may be stored in a tangible computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

What is claimed is:

1. A method for activating a bolus advisor feature of an application program executed on a mobile device, the method comprising:
    receiving, by the application program, an activation code to activate the bolus advisor feature of the application program, wherein the activation code includes (i) an identifier that identifies the bolus advisor feature to be activated and (ii) one or more parameters associated with a prescription;
    in response to the application program receiving the activation code, transmitting, by the application program, the activation code via a network from the mobile device to a server;
    in response to the application program transmitting the activation code to the server, receiving, by the application program, an authorization code from the server, wherein the authorization code indicates a validity of the activation code;
    activating, by the application program, the bolus advisor feature using the activation code, the activation being performed in response to the activation code being valid;
    configuring, by the application program, the activated bolus advisor feature using at least one of the one or more parameters associated with the prescription;
    generating, using the activated bolus advisor feature, bolus dosage data based on the one or more parameters associated with the prescription; and
    communicating, using the application program, the bolus dosage data generated based on the one or more parameters associated with the prescription from the mobile device to an insulin pump,
    wherein by including the one or more parameters associated with the prescription in the activation code:
    the bolus advisor feature automatically configures itself based on the one or more parameters included in the activation code;

the one or more parameters associated with the prescription cannot be manually altered;
the one or more parameters and the bolus dosage data generated based on the one or more parameters remain valid and in effect for the duration for which the activation code remains valid or until a new activation code is obtained, whichever occurs first; and
a new activation code has to be requested and acquired each time the bolus dosage data needs to be changed.

2. The method of claim 1, wherein the authorization code indicates that the activation code is valid in response to confirming that:
the activation code is received from the application program and not from any other application program;
the activation code is for use in a country where the application program is being used;
the activation code has not been used before; and
the activation code has not been disabled as a result of being lost or stolen.

3. The method of claim 1, wherein the authorization code includes the following:
a country code indicating a country in which the activation code is to be used;
the identifier that identifies the bolus advisor feature;
the activation code;
status indicating whether the activation code is valid; and
a time stamp indicating date and time when the activation code is validated.

4. The method of claim 1, wherein the activation code includes an alphanumeric string prefixed with a country code and the identifier that identifies the bolus advisor feature, wherein the alphanumeric string includes four alphanumeric characters, and wherein the country code includes two characters, and wherein the identifier includes one numeral.

5. The method of claim 1, wherein the activation code is valid for a predetermined time period and expires at an end of the predetermined time period.

6. The method of claim 1, wherein the one or more parameters associated with the prescription include a set of parameters that are paired with the activation code and that are used to setup the activated bolus advisor feature of the application program.

7. The method of claim 6, wherein the set of parameters includes:
a target range, which includes acceptable upper and lower blood glucose levels when fasting or before a meal;
meal rise, which accommodates an expected rise in blood glucose levels in response to food intake;
a carb ratio, which is an amount of insulin necessary to account for a specified amount of carbohydrates;
an insulin sensitivity, which is an amount of insulin necessary to lower blood glucose levels by a specified amount; and
a maximum bolus, which is a maximum amount of insulin to be delivered at one time.

8. The method of claim 1, wherein the one or more parameters associated with the prescription include a set of parameters that are not paired with the activation code and that are used to generate bolus dosage data, and wherein the set of parameters includes one or more of the following:
a snack size, which defines a threshold of carbohydrates above which a meal rise is triggered;
an offset time, which is a length of time after a bolus is administered until a reduction in blood glucose levels begins;
an acting time, which is a length of time insulin is expected to be effective at lowering blood glucose levels;
insulin increment, which a unit or a fraction of a unit of insulin; and
hypo, which is a setting below which blood glucose levels are considered hypoglycemic.

9. A method for activating a bolus advisor feature of an application program executed on a mobile device, the method comprising:
receiving, by a healthcare professional, an activation code from a server to activate the bolus advisor feature of the application program, wherein the activation code includes (i) a country code of a country where the activation code is to be used, (ii) an identifier that identifies the bolus advisor feature to be activated, and (iii) an alphanumeric string;
in response to the healthcare professional receiving the activation code from the server, receiving, by the application program, the activation code, wherein the activation code received by the application program from the healthcare professional further includes one or more parameters associated with a prescription from the healthcare professional;
in response to the application program receiving the activation code, transmitting, by the application program, the activation code via a network from the mobile device to the server;
in response to the application program transmitting the activation code to the server, receiving, by the application program, an authorization code from the server, wherein the authorization code indicates whether the activation code is valid;
activating, by the application program, the bolus advisor feature using the activation code, the activation being performed in response to the activation code being valid;
configuring, by the application program, the activated bolus advisor feature using at least one of the one or more parameters associated with the prescription;
generating, using the activated bolus advisor feature, bolus dosage data based on the one or more parameters associated with the prescription; and
communicating, using the application program, the bolus dosage data generated based on the one or more parameters associated with the prescription from the mobile device to an insulin pump, wherein by including the one or more parameters associated with the prescription in the activation code:
the bolus advisor feature automatically configures itself based on the one or more parameters included in the activation code;
the one or more parameters associated with the prescription cannot be manually altered;
the one or more parameters and the bolus dosage data generated based on the one or more parameters remain valid and in effect for the duration for which the activation code remains valid or until a new activation code is obtained, whichever occurs first; and
a new activation code has to be requested and acquired each time the bolus dosage data needs to be changed.

10. The method of claim 9, wherein the authorization code indicates that the activation code is valid in response to confirming that:
the activation code is received from the application program and not from any other application program;

the activation code is for use in the country where the application program is being used;

the activation code has not been used before; and the activation code has not been disabled as a result of being lost or stolen.

11. The method of claim 9, wherein the authorization code includes the following:

the country code indicating the country in which the activation code is to be used;

the identifier that identifies the bolus advisor feature;

the activation code;

status indicating whether the activation code is valid; and a time stamp indicating date and time when the activation code is validated.

12. The method of claim 9, wherein the alphanumeric string includes four alphanumeric characters, wherein the country code includes two characters, and wherein the identifier includes one numeral.

13. The method of claim 9, wherein the activation code is valid for a predetermined time period and expires at an end of the predetermined time period.

14. The method of claim 9, wherein the one or more parameters associated with the prescription include a set of parameters that are paired with the activation code and that are used to setup the activated bolus advisor feature of the application program.

15. The method of claim 14, wherein the set of parameters includes:

a target range, which includes acceptable upper and lower blood glucose levels when fasting or before a meal;

meal rise, which accommodates an expected rise in blood glucose levels in response to food intake;

a carb ratio, which is an amount of insulin necessary to account for a specified amount of carbohydrates;

an insulin sensitivity, which is an amount of insulin necessary to lower blood glucose levels by a specified amount; and a maximum bolus, which is a maximum amount of insulin to be delivered at one time.

16. The method of claim 9, wherein the one or more parameters associated with the prescription include a set of parameters that are not paired with the activation code and that are used to generate bolus dosage data, and wherein the set of parameters includes one or more of the following:

a snack size, which defines a threshold of carbohydrates above which a meal rise is triggered;

an offset time, which is a length of time after a bolus is administered until a reduction in blood glucose levels begins;

an acting time, which is a length of time insulin is expected to be effective at lowering blood glucose levels;

insulin increment, which a unit or a fraction of a unit of insulin; and hypo, which is a setting below which blood glucose levels are considered hypoglycemic.

* * * * *